(12) United States Patent
Rana et al.

(10) Patent No.: US 11,297,869 B2
(45) Date of Patent: Apr. 12, 2022

(54) BOTANICAL MODULATOR OF METABOLIC DISORDERS

(71) Applicant: Innophos, Inc., Cranbury, NJ (US)

(72) Inventors: Jatinder Rana, Grand Rapids, MI (US); Kylie Mitchell, Pennington, NJ (US)

(73) Assignee: Innophos, LLC, Cranbury, NJ (US)

( * ) Notice: Subject to any disclaimer, the term of this patent is extended or adjusted under 35 U.S.C. 154(b) by 0 days.

(21) Appl. No.: 17/158,693

(22) Filed: Jan. 26, 2021

(65) Prior Publication Data

US 2021/0186076 A1    Jun. 24, 2021

Related U.S. Application Data

(62) Division of application No. 16/515,101, filed on Jul. 18, 2019, now Pat. No. 10,932,485.

(60) Provisional application No. 62/725,448, filed on Aug. 31, 2018.

(51) Int. Cl.
*A23L 33/135*    (2016.01)
*A61K 36/185*    (2006.01)

(52) U.S. Cl.
CPC .......... *A23L 33/135* (2016.08); *A61K 36/185* (2013.01)

(58) Field of Classification Search
None
See application file for complete search history.

(56) References Cited

U.S. PATENT DOCUMENTS 10,932,485 B2 *   3/2021   Rana .................... A61P 3/06

* cited by examiner

*Primary Examiner* — Susan Hoffman
(74) *Attorney, Agent, or Firm* — David LeCroy

(57) ABSTRACT

Plant-based inhibitors of MMP-9 that also function as PPAR-γ agonists, and the use of such plant-based inhibitors/agonists in modulating metabolic disorders is disclosed. The plant-based inhibitor/agonist is at least an extract obtained from the genus *Anacardium*.

5 Claims, 5 Drawing Sheets

HPCL chromatogram of E1 at 275 nm wavelength

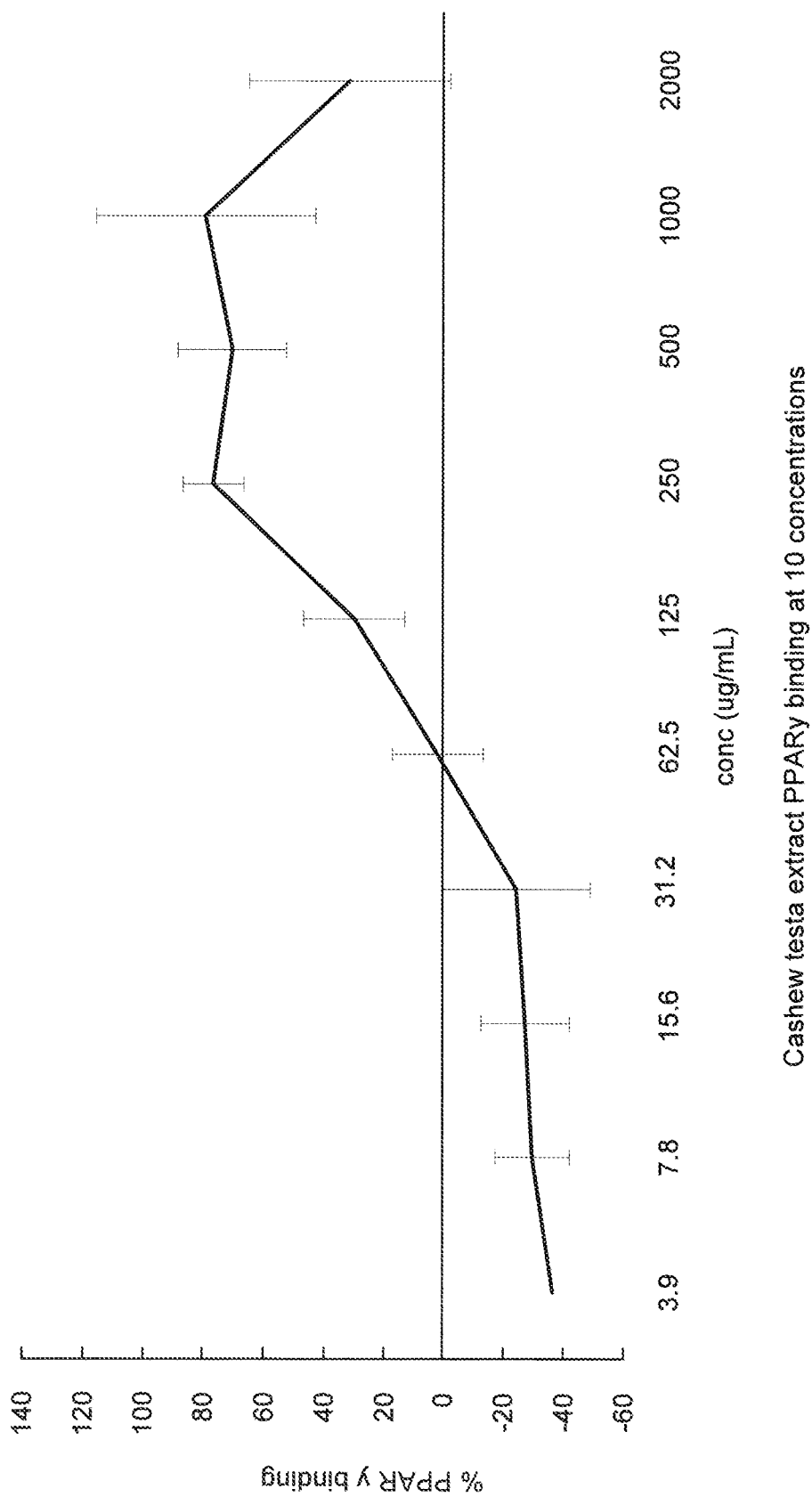

BOTANICAL MODULATOR OF METABOLIC DISORDERS

CROSS REFERENCE TO RELATED APPLICATIONS

The present application is a divisional application of U.S. patent application Ser. No. 16/515,101, filed 18 Jul. 2019 (now U.S. Pat. No. 10,932,485), which claims the benefit of U.S. Patent Application No. 62/725,448, filed 31 Aug. 2018, the disclosure of which is incorporated herein in its entirety by reference.

BACKGROUND OF THE INVENTION

Field of the Invention

The present invention generally relates to MMP-9 inhibitors and PPAR-γ agonists, and more particularly to plant-based inhibitors of MMP-9 that also function as PPAR-γ agonists, and the use of such plant-based inhibitors/agonists in modulating one or more metabolic disorders.

Under normal circumstances, extracellular matrix ('ECM') synthesis and degradation is tightly regulated. While planned degradation of ECM is an important feature of tissue repair and remodeling, uncontrolled changes of the ECM are associated with many diseases such as inflammation, cancer, and cardiovascular dysfunction. Among the cardiovascular diseases, myocardial infarction ('MI') is one of the most highly prevalent heart conditions in the United States. It is linked to long term complication and high mortality rate as a result of progression of post myocardial infarction remodeling to congestive heart failure. Matrix metalloproteinases ('MMPs') are among the key enzymes that play a crucial role in the remodeling of cardiac ECM. MMPs are a family of structurally related, zinc-dependent endopeptidases that degrade several components of the ECM, with their increased expression and/or activity associated with various pathophysiological processes. In particular, MMP-9 (also known as Gelatinase B) plays a major role in myocardial ECM remodeling. MMP-9 has consistently been found to increase in the early times post-MI, and its levels positively correlated with heart failure severity. Hence, reducing the expression level and/or activity of MMP-9 could have beneficial effects in cardiovascular health.

MMP-9 is also one of the enzymes involved in the degradation of articular cartilage matrix. Cartilage is the main component of articular structure and consists of chondrocytes that are embedded in a dense and highly organized ECM. ECM is synthesized by the chondrocytes and is composed of a collagenous network that primarily contains type II collagen, along with glycosaminoglycans ('GAGs') and associated proteoglycans. Collagen forms a fibrillar network and provides the cartilage matrix with tensile strength whereas aggrecan is the major cartilage proteoglycan, drawing water into the matrix and allowing it to resist compression. Along with aggrecan breakdown, degradation of collagen is a central feature of arthritis. Pro-inflammatory cytokines such as tumor necrosis factor alpha ('TNF-α'), interleukin 1 ('IL-1') and IL-6 are known to play important roles in cartilage matrix degradation in the articular cartilage through a cascade of events that lead to stimulation of aggrecanase and matrix metalloproteinase (such as MMP-9) production. A reduction in MMP-9 by a botanical extract would indicate the extract's ability to contribute to healthier joint structure through maintenance of intact cartilage.

MMP-9 seems to be involved in the enzymatic process of many pathological conditions. Cancer (breast, pancreas, lung, bladder, colorectal, ovarian, prostate and brain); periodontal disease (periodontitis and gingivitis); secondary complications of diabetes (plaque formation in atherosclerosis); delayed wound healing (venous leg ulcers); inflammatory bowel disease complications (Crohn's disease); neuroinflammation (multiple sclerosis); and gastric ulcer are a few of numerous human ailments affected by the presence of this enzyme. Therefore, modulating the expression and/or activity of MMP-9 is vital to correcting many chronic and acute diseases.

Insulin resistance and impaired glucose tolerance are two key imbalances in metabolic syndrome with strong association to abdominal obesity, hypertension, and dyslipidemia. People affected by these disorders have a greater risk of developing cardiovascular diseases, type II diabetes, chronic low-grade local tissue inflammation and increased susceptibility to other disease conditions such as fatty liver, sleep disturbances and cancer. Through the years, several anti-hyperglycemic products have been developed to combat these challenges by targeting ways to increase insulin secretion, sensitize tissues and organs for insulin, increase glucose uptake and transport, and decrease absorption of carbohydrates from the gut. Among these targets, for example, Peroxisome proliferator activated receptor gamma ('PPAR-γ') influences insulin sensitivity of peripheral tissues by controlling the expression of many factors secreted from adipose tissue, such as adiponectin, leptin, resistin and tumor necrosis factor-alpha (TNF-α). PPAR-γ can also directly upregulate glucose transporter type 4 (Glut4) and hence modulate glucose homeostasis.

PPARs are ligand-activated transcription factors that regulate target gene expression. Following endogenous or exogenous agonist binding, PPAR receptors heterodimerize with retinoid X receptor (RXR) and bind to PPAR response elements (PPREs) located in the promoter region of target genes resulting in regulation of gene expression. In addition to effects on maintenance of metabolic homeostasis, PPARs regulate the expression of genes involved in lipid metabolism, adipogenesis, and inflammation.

There are at least three PPAR subtypes (α, β and γ) with diverse tissue expression, suggesting that each of these subtypes may have specific functions. Among them, PPAR-γ is known to have two isoforms—PPAR-γ1 and PPAR-γ2. PPAR-γ1 is abundantly expressed in adipose tissue, large intestine, and hematopoietic cells, and to a lower extent in kidney, liver, muscles, pancreas, and small intestine. In contrast, PPAR-γ2 is limited to white and brown adipose tissues.

Activation of PPAR-γ is one of the key steps in the process of differentiation of pre-adipocyte precursor cells into adipocytes with an ultimate effect on the modulation of glucose metabolism. For instance, the potent exogenous agonists of PPAR-γ—the thiazolidinediones (a/k/a 'TZDs' or glitazones, e.g., troglitazone, rosiglitazone, and pioglitazone)—are known to improve insulin responsiveness, increase glucose uptake and lipid storage of adipocytes through this pathway, making them a good intervention choice for diabetes mellitus.

Phytomedicine plays an important role in the management of most of these diseases, with plants being a potential source of natural modulators of metabolic disorders. Consequently, there is a growing research interest in plants that contain modulators and health-promoting phytoconstituents as potential therapeutic agents. Medicinal plants provide a safe, cost-effective, ecological alternative to chemical modulators, which can be toxic on prolonged exposure.

The cashew tree (*Anacardium occidentale* Linn) is originally from the Amazon, and has subsequently been transplanted to India, Eastern Africa, and other countries for cultivation. The tree produces a very peculiar apple or fruit in the form of a swollen peduncle. Externally at the end of this peduncle the cashew nut grows in its own grey colored kidney-shaped hard shell. This shell has a soft leathery outer skin and a thin hard inner skin referred to as the husk or testa, which surrounds the kernel. Between these two skins is a honeycomb structure containing the cashew nut shell liquid. This liquid comprises anacardic acid, cardanol, and cardol, among other ingredients. Anacardic acid is a salicylic acid, while cardanol and cardol are substituted phenols.

The various parts of the fruit have been studied for their uses. In addition to being an edible food, the juice from the cashew apple is used in beverages, while the fruit extract has shown benefit in weight management. Cashew nut shell liquid has been extracted for various industrial and agricultural applications, including friction linings, paints, laminating resins, rubber compounding resins, cashew cements, polyurethane based polymers, surfactants, epoxy resins, foundry chemicals, chemical intermediates, insecticides, and fungicides. Cashew testa has been used in tanning materials.

As part of a healthy lifestyle and a well-balanced, wholesome diet, supplementation is recognized as an important means of modulating various metabolic disorders. As noted above, there is a need for effective, nontoxic, natural compounds with such modulating activity. The present invention provides one such solution.

BRIEF SUMMARY OF THE INVENTION

The present invention provides a botanical extract comprising catechins, wherein the extract has been standardized to a catechin content of about 15.0 w/w % or greater, based on total weight of the extract, wherein the botanical extract exhibits modulatory properties for one or more metabolic disorders, and wherein the botanical extract comprises at least an extract obtained from the genus *Anacardium*. Preferably, the botanical extract is at least an extract obtained from *Anacardium occidentale* L. In particular, the botanical extract is obtained from at least the testa of the fruit of *Anacardium occidentale* L.

In another embodiment, the present invention is direct towards a composition comprising the botanical extract of the testa of the seed of *Anacardium occidentale* L., wherein the botanical extract exhibits modulation of one or more metabolic disorders. Preferably, the botanical extract is present in the composition in an amount of about 1.0 µg/mL or greater; more preferably, in an amount of about 1.0 µg/mL to about 2000.0 µg/mL; even more preferably, in an amount of about 50.0 µg/mL to about 500.0 µg/mL. In one aspect, the composition exhibits MMP-9 inhibition. In such instances, the botanical extract is present in an amount of about 1.0 µg/mL to about 2000.0 µg/mL. In another aspect, the composition exhibits PPAR-γ agonist activity. In such instances, the botanical extract is present in an amount of about 50.0 µg/mL to about 2000.0 µg/mL.

In a further embodiment, the present invention provides a dietary supplement having modulatory properties for one or more metabolic disorders comprising a cashew testa extract in a therapeutically effective amount. Preferably, the cashew testa extract is present in the supplement in an amount of about 1.0 µg/mL or greater.

The present invention further provides a modulating one or more metabolic disorders in a subject by administering a composition comprising the botanical extract of the testa of the seed of *Anacardium occidentale* L. at a concentration of about 1.0 µg/mL to about 2000.0 µg/mL.

BRIEF DESCRIPTION OF THE SEVERAL VIEWS OF THE DRAWINGS

FIG. 4 is a graph illustrating percentage Peroxisome proliferator activated receptor gamma (PPAR-γ) ligand binding using cashew testa extract at various concentrations.

DETAILED DESCRIPTION OF THE INVENTION

Figure 1:
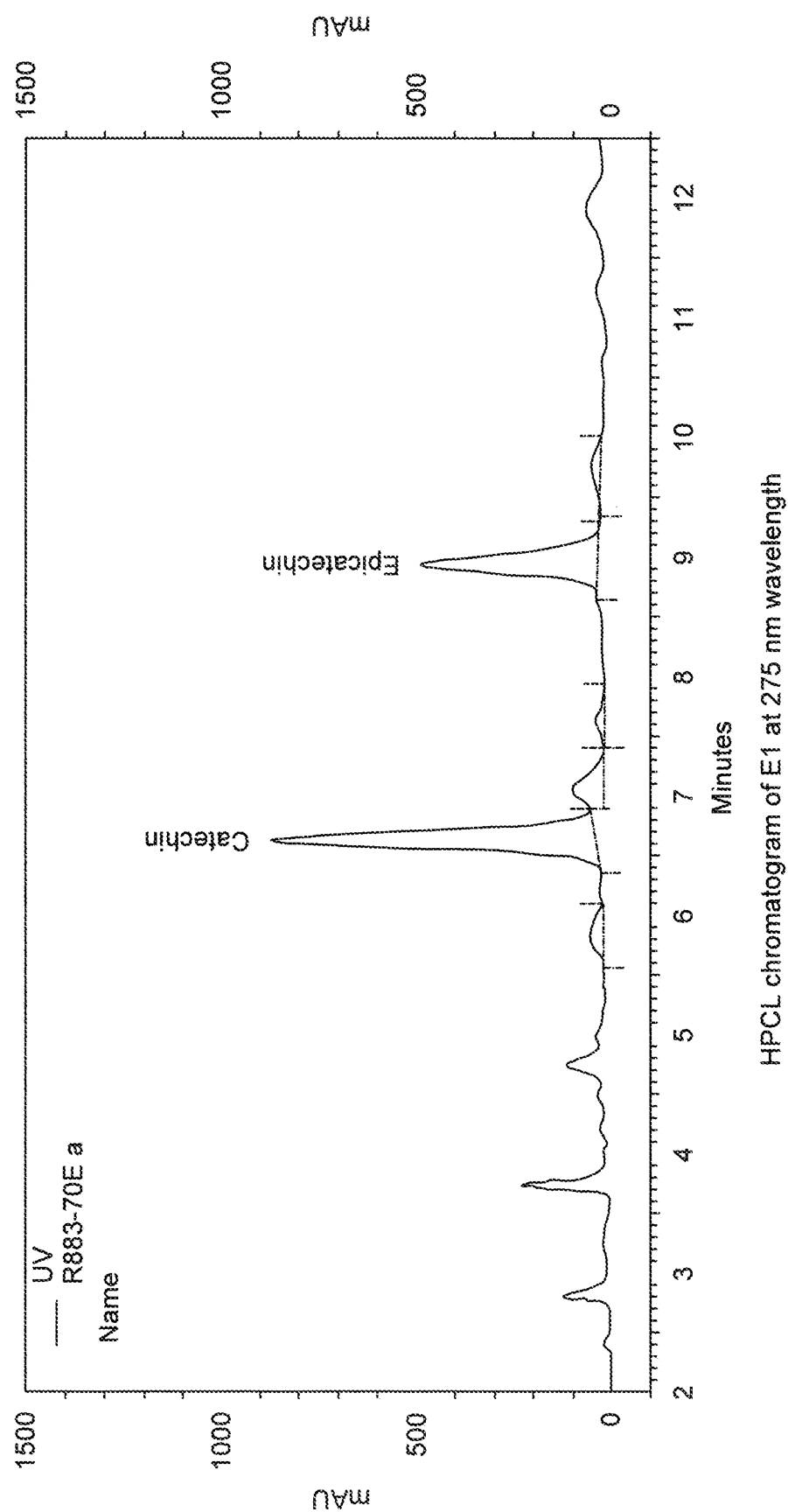
FIG. 1 an HPLC chromatogram of cashew testa extract at 275 nm wavelength over a retention time of from 0 minutes (start) to 20 minutes.

The present invention is based on the surprising discovery that the testa of the cashew (*Anacardium*) is substantially high in certain flavonoids. In particularly, it has been discovered that the extract of cashew testa comprises catechin and epicatechin as major components, as well as procyanidins. Data noted herein demonstrates that cashew testa extract may have applications in modulating one or more metabolic disorders.

For the present application, the term "composition" refers to a product that treats, improves, promotes, increases, manages, controls, maintains, optimizes, modifies, reduces, inhibits, or prevents a particular condition associated with a natural state, biological process or disease or disorder. For example, a composition improves the inhibition of metastasis and/or reduces inflammation, and the like in a subject. The term composition includes, but is not limited to, pharmaceutical (i.e., drug), over-the counter (OTC), cosmetic, food, food ingredient or dietary supplement compositions that include an effective amount of an extract, at least one component thereof, or a mixture thereof. Exemplary compositions include cream, cosmetic lotion, pack or powder, or as an emulsion, lotion, liniment foam, tablets, plasters, granules, or ointment. Compositions can also include beverages, for example, beverages infused with an effective amount of an extract, or a tea satchel containing an effective amount of an extract. Non-limiting examples of food compositions containing an effective amount of an extract include baked goods, protein powders, meat products, dairy products, and confectionary.

As used herein, the term "extract" or "botanical extract" refers to a solid, viscid, or liquid substance or preparation that includes one or more active ingredients of a substance of at least the plant *Anacardium* (e.g., *Anacardium humile, Anacardium othonianum, Anacardium giganteum, Anacardium nanum, Anacardium negrense,* and/or *Anacardium occidentale*), preferably *Anacardium occidentale* L. Preferably, the active ingredient is derived from the extract of the testa of the cashew. The extract can be prepared using a solvent such as water, lower alcohols of 1 to 4 carbon atoms (e.g., methanol, ethanol, butanol, etc.), ethylene, acetone, hexane, ether, chloroform, ethylacetate, butylacetate, dichloromethane, N,N-dimethylformamide ('DMF'), dimethylsulfoxide ('DMSO'), 1,3-butylene glycol, propylene glycol, and combinations thereof, but also a fraction of the crude extract in such a solvent. So long as it assures the extraction and preservation of the active ingredient(s), any extraction method may be employed.

As used herein, the term "effective amount" or "therapeutically effective amount" of a pure compound, composition, extract, extract mixture, component of the extract, and/or active agent or ingredient, or a combination thereof refers to an amount effective at dosages and for periods of time sufficient to achieve a desired result. For example, the "effective amount" or "therapeutically effective amount" refers to that amount of a pure compound, composition, extract, botanical extract, extract mixture, botanical extract mixture, component of the extract, and/or active agent or ingredient, or a combination thereof of this invention which, when administered to a subject (e.g., mammal, such as a human), is sufficient to effect treatment, such as improving the inhibition of oxidation and/or reducing inflammation, and the like in a subject. The amount of a composition, extract, botanical extract, extract mixture, botanical extract mixture, component of the extract, and/or active agent or ingredient of this disclosure that constitutes an "effective amount" or "therapeutically effective treatment" will vary depending on the active agent or the compound, the condition being treated and its severity, the manner of administration, the duration of treatment, or the age of the subject to be treated, but can be determined routinely by one of ordinary skill in the art having regard to his own knowledge and to this disclosure.

The term "pharmaceutically acceptable" means those drugs, medicaments, extracts or inert ingredients, which are suitable for use in contact with the tissues of humans and lower animals without undue toxicity, incompatibility, instability, irritation, and the like, commensurate with a reasonable benefit/risk ratio.

The terms "administer", "administered", "administers", and "administering" are defined as providing a composition to a subject via a route known in the art, including but not limited to intravenous, intra-arterial, oral, parenteral, buccal, topical, transdermal, rectal, intramuscular, subcutaneous, intraosseous, transmucosal, or intraperitoneal routes of administration. In preferred embodiments, oral routes of administering a composition are suitable.

As used herein, the term "subject" or "individual" includes mammals to which a composition may be administered. Non-limiting examples of mammals include humans, non-human primates, canines, felines, equines, bovines, rodents (including transgenic and non-transgenic mice) or the like. In some embodiments, the subject is a non-human mammal, and in some embodiments, the subject is human.

As used herein, the term "carrier" refers to a composition that aids in maintaining one or more plant extracts in a soluble and homogeneous state in a form suitable for administration, which is nontoxic and which does not interact with other components in a deleterious manner.

The term "modulation" or "modulator" as used herein generally refers to a substance that indirectly influences (or modulates) one or more metabolic disorders.

The term "metabolic disorder" as used herein refers to abnormal chemical reaction(s) that alter normal metabolic process(es). Non-limiting examples of metabolic disorders include glucose metabolism disorders, DNA repair-deficiency disorders, lipid metabolism disorders, malabsorption disorders, and calcium metabolism disorders. Symptoms of such disorders are often found in a cluster of conditions referred to as metabolic syndrome, including hypertension (increase blood pressure), abdominal obesity (excess body fat around the waist), and dyslipidemia (abnormal cholesterol or triglyceride levels), that occur together, increasing one's risk of heart disease, stroke, and diabetes.

Unless indicated otherwise, all proportions and percentages recited throughout this disclosure are by weight.

The present invention provides a plant-based extract capable of modulating one or more metabolic disorders. More particularly, the present invention is directed towards a botanical extract of the cashew testa from the genus *Anacarium*. Such botanical extracts have been found to be capable of inhibiting MMP-9 and acting as an agonist for PPAR-γ, thereby limiting adverse enzyme activity in the case of MMP-9 inhibition, and/or promoting ligand binding when acting as an agonist for PPAR-γ. PPAR-γ influences insulin sensitivity of peripheral tissues by controlling the expression of many factors secreted from adipose tissue such as adiponectin, leptin, resistin and tumor necrosis factor-alpha (TNF-α). PPAR-γ can also directly upregulate glucose transporter type 4 (Glut4) and hence modulate glucose homeostasis. By limiting MMP-9 and/or promoting PPAR-γ activity, one or more metabolic disorders can be mitigated, for example, inflammation, metastasis, and/or insulin sensitivity. Further, by limiting MMP-9 and/or promoting PPAR-γ activity, one or more symptoms of metabolic syndrome may be mitigated, including hypertension, obesity, and/or dyslipidemia.

Useful botanical extracts capable of inhibiting MMP-9 and/or acting as an agonist for PPAR-γ according to the present invention include botanical extracts from the genus *Anacardium*. More particularly, the plant-based inhibitor is a botanical extract chosen from one or more of the species *Anacardium humile, Anacardium othonianum, Anacardium giganteum, Anacardium nanum, Anacardium negrense*, and/or *Anacardium occidentale*. Preferably, the botanical extract is from the species *Anacardium occidentale* Linn. In one embodiment, the botanical extract is from the testa of the species *Anacardium occidentale*.

Compositions capable of inhibiting MMP-9 and/or acting as an agonist for PPAR-γ according to the present invention may include one or more compounds that may function as active ingredients. The compound may be a component of the botanical extract. For example, the compound can be a phytochemical present in the plant from which the plant extract is obtained. The compound may be at least partially responsible for inhibiting MMP-9 and/or acting as an agonist for PPAR-γ. The compound can be any compound capable of inhibiting MMP-9 and/or acting as an agonist for PPAR-γ. In one embodiment, the compound is chosen from the phytochemicals catechins, epicatechins, and/or procyanidins (e.g., A, B, trimer, tetramer).

Generally, one or more parts of a plant can be used to produce a plant extract including, but not limited to, the root, the stem, the leaf, the flower, the fruit, the seed, and the testa of the seed. In the present invention, at least the testa of the seed is used—alone or with other plant parts—to produce the plant extract. The testa from the *Anacardium* plant can be commercially obtained from various sources. The extract of the cashew testa can be obtained using any suitable extraction technique.

In this regard, one or more parts of the plant, particularly the testa of the plant, can be collected and milled. Thereafter, the milled material can be extracted using a suitable solvent. The solvent can be removed in a concentration step. For example, the extracted material can be screened or filtered to create a supernatant and a cake. The cake can be pressed to remove a substantial portion of the liquid, which can be added to the supernatant. The cake can then be dehydrated and used as a fiber source. The supernatant can be distilled to remove the solvent or a portion thereof, to form a plant extract liquid concentrate. The removed solvent can be recycled. The concentrate can be dried (e.g., by spray drying) to provide a dried plant extract. This dried plant extract can be assayed and/or standardized as described herein. Preferably, the dried plant extract is derived from *Anacardium occidentale*, particularly the testa of the plant *Anacardium occidentale*.

Suitable solvents for the extraction process include water, alcohol, or mixtures thereof. Exemplary alcoholic solvents include, but are not limited to, $C_1$-$C_7$ alcohols (e.g., methanol, ethanol, propanol, isopropanol, and butanol), hydroalcohols or mixtures of alcohol and water (e.g., hydroethanol), polyhydric alcohols (e.g., propylene glycol and butylene glycol), and fatty alcohols. Any of these alcoholic solvents can be used in the form of a mixture. In one embodiment, the plant extract is extracted using ethanol, water, or a combination thereof (e.g., a mixture of about 70% ethanol and about 30% water). In another embodiment, the plant extract is extracted using only water.

In one embodiment, the plant extract can be obtained using an organic solvent extraction technique. In another embodiment, solvent sequential fractionation can be used to obtain the plant extract. Total hydro-ethanolic extraction techniques can also be used to obtain the plant extract. Generally, this is referred to as a lump-sum extraction.

Total ethanol extraction can also be used. This technique uses ethanol as the solvent. This extraction technique can generate a plant extract having fat soluble and/or lipophilic compounds in addition to water soluble compounds.

Another example of an extraction technique that can be used to obtain the plant extract is supercritical fluid extraction ('SFE'). In this extraction procedure, the material to be extracted may not be exposed to any organic solvents. Rather, carbon dioxide can be used as the extraction solvent—with or without a modifier—in super-critical conditions (>31.3° C. and >73.8 bar). Those skilled in the art will appreciate that temperature and pressure conditions can be varied to obtain the best yield of extract. This technique can generate an extract of fat soluble and/or lipophilic compounds, similar to a total hexane and ethyl acetate extraction technique.

The plant extract generated in the process can include a broad variety of phytochemicals present in the extracted material. The phytochemicals can be fat soluble or water soluble. Following collection of the extract solution, the solvent can be evaporated, resulting in the extract.

The plant extract can be standardized to a specified amount of a particular compound. For example, the plant extract can be standardized to a specified amount of an active ingredient or phytochemical present in the extract. In one embodiment, the plant extract is standardized to a catechin content of about 15.0 wt % or greater, based on total weight of the extract.

The amount of plant extract present in the MMP-9 inhibitor and/or PPAR-γ agonist composition can depend upon several factors, including the desired level of MMP-9 inhibition and/or PPAR-γ increase in activity, the MMP-9 inhibition and/or PPAR-γ increase in activity level of a particular plant extract or component thereof, and other factors. Preferably, the plant extract is present in an amount of from about 0.005 wt % or greater, for example, from about 0.005 wt % to about 99.00 wt %, based on total weight of the composition.

The MMP-9 inhibitor and/or PPAR-γ agonist composition can include one or more acceptable carriers. The carrier can aid in enabling incorporation of the plant extract into an MMP-9 inhibitor and/or PPAR-γ agonist composition having a suitable form for administration to a subject. A wide number of acceptable carriers are known in the art, and the carrier can be any suitable carrier. The carrier is preferable suitable for administration to animals, including humans, and can be able to act as a carrier without substantially affecting the desired activity of the plant extract and/or any active ingredient. The carrier can be chosen based upon the desired administration route and dosage form of the composition.

Suitable dosage forms include liquid and solid forms. In one embodiment, the composition is in the form of a gel, a syrup, a slurry, or a suspension. In another embodiment, the composition is in a liquid dosage form such as a drink shot or a liquid concentrate. In a further embodiment, the composition is present in a solid dosage form, such as a tablet, a pill, a capsule, a dragée, or a powder. When in liquid or solid dosage form, the composition can be in a food delivery form suitable for incorporation into food for delivery. Examples of suitable carriers for use in solid forms (particularly tablet and capsule forms) include, but are not limited to, organic and inorganic inert carrier materials such as gelatin, starch, magnesium stearate, talc, gums, silicon dioxide, stearic acid, cellulose, and the like. The carrier can be substantially inert.

As an example, silicified microcrystalline cellulose can be used as a carrier or binder. Silicified microcrystalline cellulose is a physical mixture of microcrystalline cellulose and colloidal silicon dioxide. One such suitable form of silicified microcrystalline cellulose is ProSolv SMCC® 90, available from Penwest Pharmaceutical Co., Patterson, N.J. Silicon dioxide, in addition to that provided by the silicified microcrystalline cellulose, may be added to the composition as a processing aid. For example, silicon dioxide can be included as a glidant to improve the flow of powder during compression in the manufacturing of solid dosage units, such as tablet.

In another embodiment, the carrier is at least a functional carrier such as buckwheat or spelt. By the addition of functional carriers into the composition, additional benefits may be provided such as lower glycemic index compared to standard carriers such as those mentioned above. Further, functional carriers can be allergan free (e.g., buckwheat), and by adding them into the production process, the botanical extracts of the invention may benefit from the flavonoids of these functional carriers, such as rutin and quercetin. Further, the high fiber content of these functional carriers may also facilitate and regulate intestinal transit. Finally, the added mineral benefit of selenium found in spelt may aid in metabolism.

The MMP-9 inhibitor and/or PPAR-γ agonist composition can include other inert ingredients, such as lubricants and/or glidants. Lubricants aid in the handling of tablets during manufacturing, such as during ejection from dies. Glidants improve powder flow during tablet compression. Stearic acid is an example of an acceptable lubricant/glidant.

The MMP-9 inhibitor and/or PPAR-γ agonist composition can be made in solid dosage form, such as tablets and capsules. This form provides a product that can be easily transported by an individual to a place of eating, such as a restaurant, and taken prior to, during, or after consumption of a foodstuff. The composition can be formulated into dosage units containing suitable amounts of the plant extract and/or active ingredient that permit an individual to determine an appropriate number of units to take based upon appropriate parameters, such as body weight, foodstuff size, or carbohydrate (e.g., sugar) content.

In one embodiment, the botanical extract is present in the composition in a therapeutically effective amount, such as an amount of about 1.0 μg/mL or greater, preferably from about 1.0 μg/mL to about 2000.0 μg/mL, more preferably from about 30.0 μg/mL to about 1000.0 μg/mL, even more preferably from about 50.0 μg/mL to about 500.0 μg/mL, and even more preferably from about 100.0 μg/mL to about 250.0 μg/mL. The composition can be administered as a single dose, or in multiple doses. In one example, the compound is administered in up to three doses per day. For example, the compound may be administered prior to a meal, during a meal, or after a meal. In one embodiment, the composition is a dietary supplement having MMP-9 inhibitor and/or PPAR-γ agonist properties containing cashew testa extract in a therapeutically effective amount.

The dosage can be chosen to provide a level of inhibitory effect in a single unit that may be effective for some individuals and/or some foodstuffs, while also allowing for relatively simple dosage increases to provide other levels of inhibitory effects that can be effective for other individuals and/or other foodstuffs.

The inhibiting composition can be in a form adapted for oral ingestion. This form can be configured as a single dosage form intended to provide a specified dose of the plant extract. For example, the single dosage form can be a powder, a pill, a tablet, a capsule, or a drink shot. The single dosage form can include, for example, from about 1.0 μg/mL to about 2000.0 μg/mL of the plant extract.

EXAMPLES

Examples—Materials and Chemical Profiling

Example 1—Preparation of Cashew Testa Extract Using 70% Ethanol Solvent

Dried cashew testa powder (*Anacardium occidentale*) (60 g) was loaded into three 100 ml stainless steel tubes and extracted twice using a solvent of 70% ethanol in DI water with a Thermo Scientific™ Dionex™ ASE 350 Accelerated Solvent Extractor at a temperature of 80° C. and pressure of 1500 psi. The extract solution was filtered and collected. The combined ethanol extract solution was evaporated with a rotary evaporator under vacuum to give a crude cashew testa extract.

The extraction results are provided in the following Table 1—

TABLE 1

| Extraction of cashew testa | | | |
|---|---|---|---|
| Plant Part | Plant Powder (g) | Extract Weight (g) | Extraction Yield (wt %) |
| Testa | 60 | 23.78 | 39.63% |

Example 2—Catechin Quantification of Cashew Testa Extract

Free catechins present in the cashew testa extract were determined using a C18 reversed-phase column (Luna® 5 μm C18(2) 100 Å LC Column 250×4.6 mm, available from Phenomenex®, Torrance, Calif., US) together with an Hitachi high performance liquid chromatograph with photodiode array detector ('HPLC/PDA'). For mobile phase A, the solvent was 0.10% phosphoric acid ('$H_3PO_4$') in water, and for mobile phase B, the solvent B was acetonitrile ('ACN'), which was used for elution at a flow rated of 1.0 ml/min with UV absorbance at 275 nm and a column temperature of 35° C. Catechin reference standards used were from Sigma-Aldrich Co. The reference standards were dissolved in methanol ('MeOH'): 0.1% $H_3PO_4$ (1:1 ratio) with catechin (C1251) at a concentration of 0.5 mg/ml and epicatechin (E1753) at 0.1 mg/ml. Testing samples were prepared at 2 mg/ml in 50% MeOH in 0.1% $H_3PO_4$ in a volumetric flask and sonicated until dissolved (approximately 10 minutes), and then cooled to room temperature, mixed well, and filtered through a 0.45 μm nylon syringe filter. HPLC analysis was performed by injecting a 20 μl sample into the HPLC. Table 2 below provides the gradient table of HPLC analytical method—

TABLE 2

| Gradient Table of HPLC Analytical Method | | |
|---|---|---|
| Time (min) | Mobile Phase A | Mobile Phase B |
| 0.0 | 85.0 | 15.0 |
| 7.0 | 85.0 | 15.0 |
| 12.0 | 10.0 | 90.0 |
| 16.5 | 10.0 | 90.0 |
| 16.6 | 85.0 | 15.0 |
| 24.0 | 85.0 | 15.0 |

HPLC Catechin quantification results in cashew testa extract provided a catechin content of 9.40% and an epicatechin content of 6.12%, for a total catechin content of 15.52% by weight, based on total weight of the extract. Accordingly, the cashew testa extract can be standardized to a total catechin content of about 15.00% or greater by weight, based on total weight of the extract. The HPLC chromatogram for cashew testa extract at 275 nm wavelength is provided in FIG. 1.

Example 3—Chemistry Profiling of Cashew Testa Extract

Flavonoid compounds present in the cashew testa extract were determined using ultra high pressure liquid chromatography ('HPLC') and mass spectrometry (ACQUITY® UPLC I-Class and XEVO® GS-XT-QTof system, both available from Water Corporation, Milford, Mass. USA). The column used was an ACQUITY® UPLC HSS T3 2.1×100 mm, 1.8 μm, with a column temperature of 40° C. and a sample temperature of 15° C. For the mobile phase, Solvent A was 10% acetonitrile ('ACN') in water (0.1% Formic Acid), and Solvent B was ACN. The acquisition range was 100-1500 Daltons (Da'), and the acquisition mode was electrospray ionization ('ESI') (−). Table 3 below provides the HPLC conditions—

TABLE 3

| HPLC conditions for analyzing cashew testa extract | | |
|---|---|---|
| Run Time (min) | Injection Volume (μL) | Concentration |
| 20.00 | 2.00 | 1 mg/mL |

Figure 2:
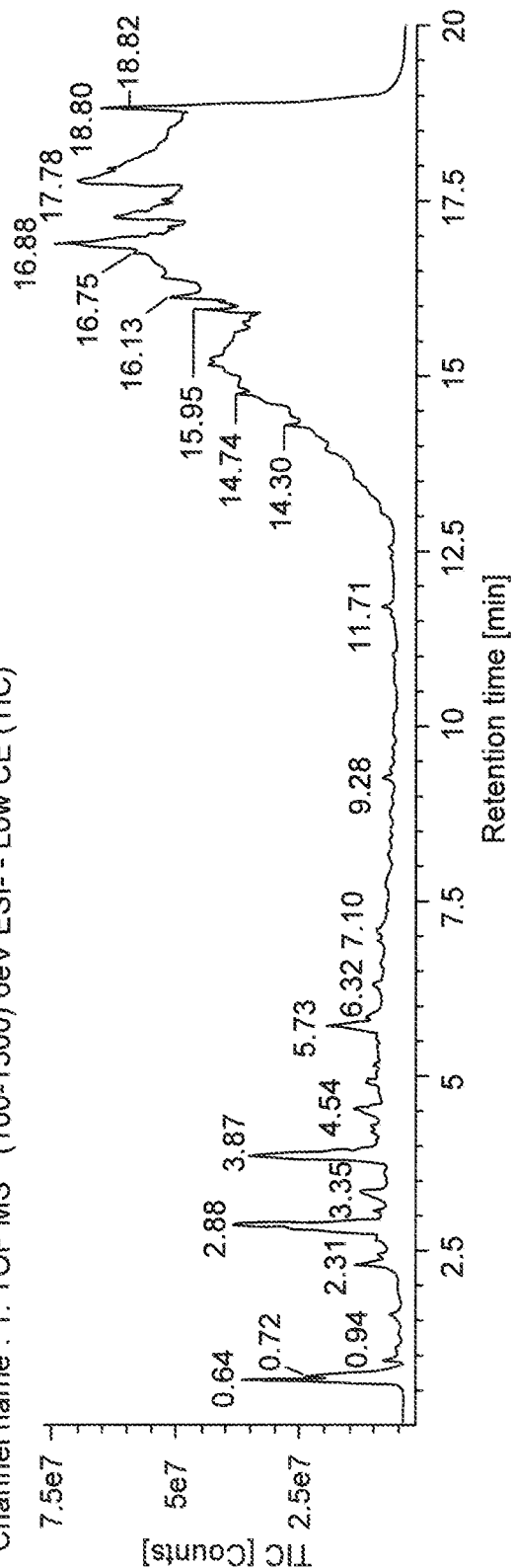
FIG. 2 is LC/MS and LC/PDA (wavelengths of 280 and 350 nm) chromatograms of cashew testa extract.
Figure 2:
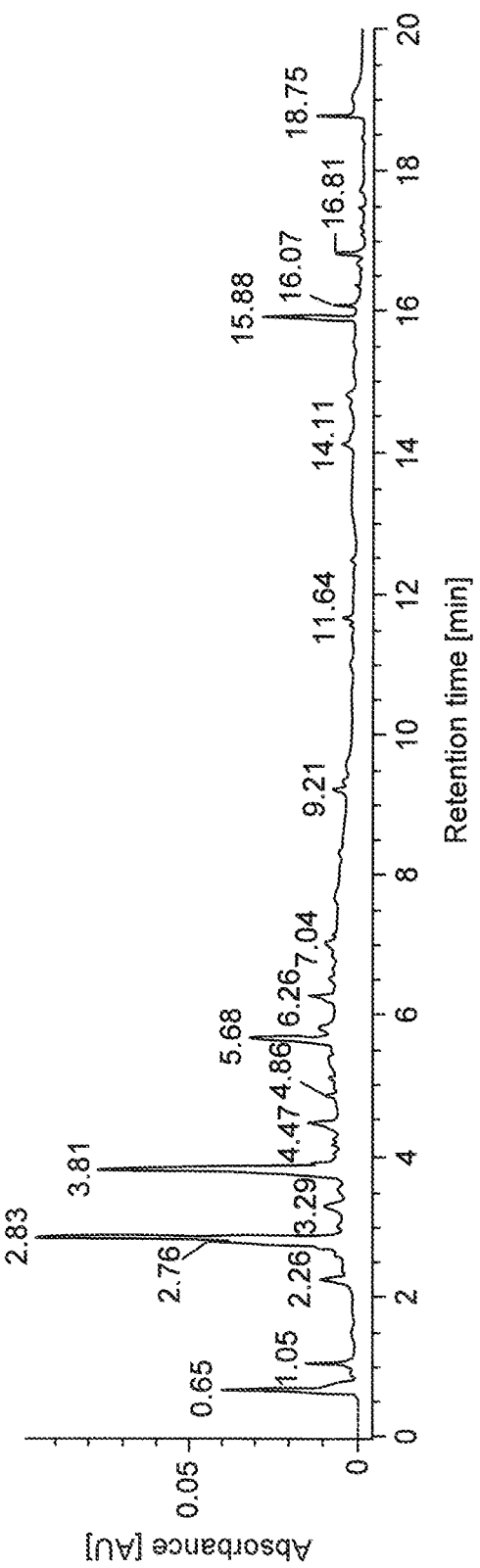
Figure 2:
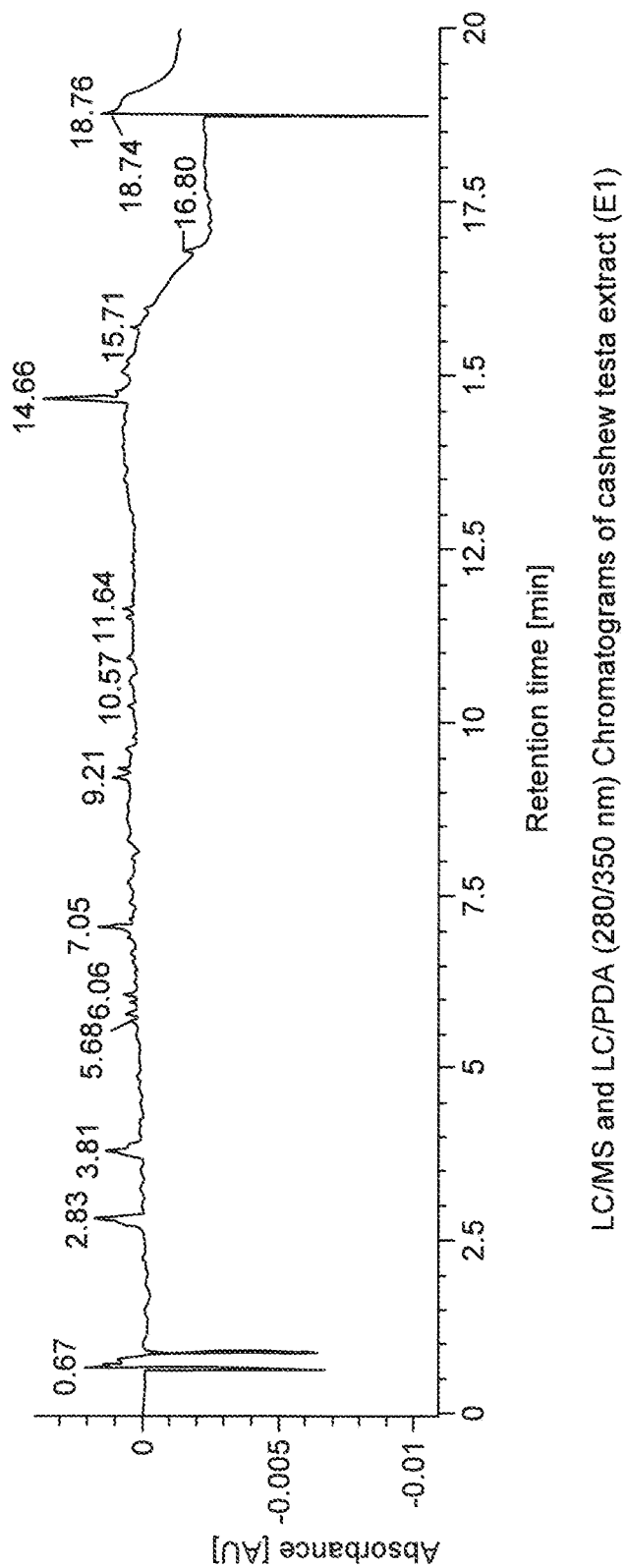

Peak identification was based on accurate mass only. Digalloyl catechin, catechin and epicatechin were identified as the major components for cashew testa extract. Procyanidins were detected in the extract as well, including A- and B-type procyanidins, procyanidin tetramer, and procyanidim trimer, with B-type procyanidins being the major component of the procyanidins. Compounds identified, in addition to those just mentioned, included digalloyl catechin, vaccihein A, 6"-p-coumaroylprunin, and dunalianoside B, among others. LC/MS and LC/PDA chromatograms of cashew testa extract obtained from the analysis are illustrated in FIG. 2.

Examples—Bioassay

Extracts of cashew testa were prepared with food-grade ethanol, and then filtered and dried as described above. Research grade reagents were used for the rest of the assay preparations. Extracts were dissolved in dimethyl sulfoxide ('DMSO') to a final concentration of 50 mg/mL, and then diluted in appropriate buffer for each bioassay to working concentrations.

Example 4—MMP-9 Inhibition

The MMP-9 Inhibitor Screening Assay Kit (Colorimetric) from abcam (Cambridge, United Kingdom; product no. ab139448) was utilized for the assay. Cashew testa extract was diluted in assay buffer to test for MMP-9 inhibition in a dose curve and added to the wells of a 96-well half-volume microplate. NNGH—a broad spectrum MMP inhibitor—was used as a positive control at 1.3 µM. The MMP-9 enzyme was diluted 1:60 in assay buffer and added to the test wells and positive and negative controls at a final concentration of 0.9 units per well. The plate was incubated at 37° C. for 30 minutes to allow the inhibitors to bind the enzyme. MMP-9 substrate was diluted 1:25 in assay buffer and added to the wells at a final concentration of 100 µM. The plate was then continuously read for absorbance at 405 nm with readings every minute for 20 minutes. The slope over the linear range (first 10 minutes) was calculated for every well and percent inhibition of the test compounds and positive control were determined using the negative (untreated) control wells as the 100% mark.

Figure 3:
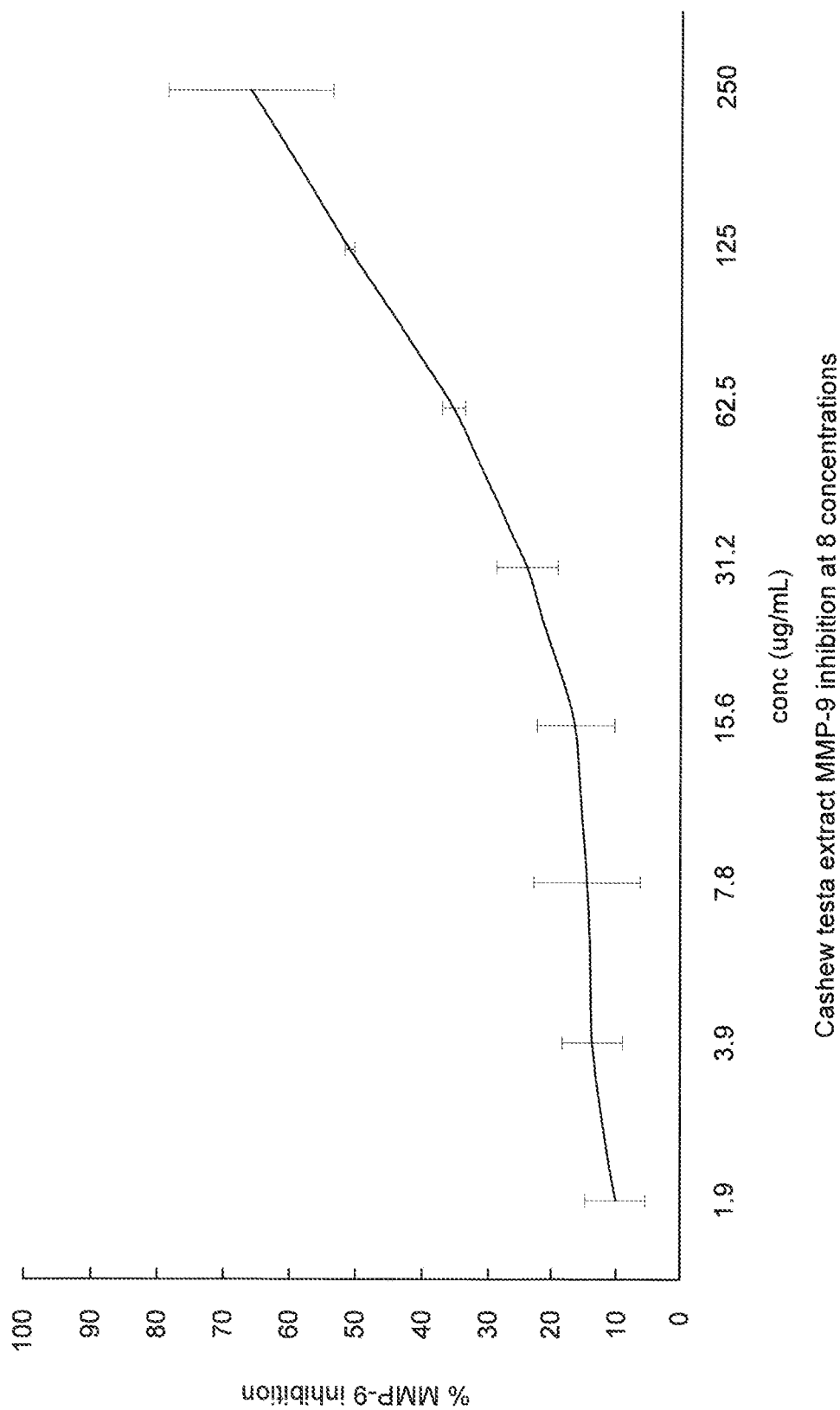
FIG. 3 is a graph illustrating percentage Matrix metalloproteinase 9 (MMP-9) inhibition using cashew testa extract at various concentrations.

Referring to FIG. 3, various degrees of MMP-9 inhibition were observed, depending on the concentration of cashew testa extract. Cashew testa extract inhibition was observed to be from about 1 µg/mL or greater, more particularly from about 1 µg/mL to at least about 250 µg/mL, even more particularly from about 15 µg/mL to about 250 µg/mL, with an $IC_{50}$ of 123 µg/mL.

Example 5—PPAR-γ Activation

The PPAR-γ Ligand Screening/Characterization Assay Kit from BioVision (product #: K437-100) to test cashew testa extract for its ability to bind and activate PPAR-γ. This assay kit relies on the displacement of a fluorescent probe bound to the PPAR-γ protein by test samples. When test samples displace the fluorescent probe and bind to PPAR-γ, there is an observable decrease in fluorescent intensity. PPAR-γ Assay Probe was diluted 1:100 in DMSO. A master mix of PPAR-γ Protein, PPAR-γ Assay Probe, PPAR-γ Assay Buffer, and DMSO (10% final concentration) was prepared and added to test samples in a 384-well black plate for a total of 25 µL per well. The plate was incubated at room temperature for 5 minutes before being read on a fluorescent plate reader at the following wavelengths: excitation—405 nm, emission—460 nm. The samples were also read in the absence of PPAR-γ Assay Probe or PPAR-γ protein, and these blank values were subtracted from the experimental values to correct for interference. Percent inhibition was calculated as the difference in fluorescence intensity between the untreated control—which had 100% binding of fluorescent probe to PPAR-γ protein—and test samples divided by the value of the untreated control and expressed as a percent.

Referring to FIG. 4, various degrees of intensity in PPAR-gamma ligand binding activities was observed for the extract. Cashew testa extract was tested at 10 different concentrations (3.9, 7.8, 15.6, 31.2, 62.5, 125, 250, 500, 1000, and 2000 µg/mL). Cashew testa extract activation was observed to be from about 50.0 µg/mL to at least about 2000 µg/mL, more particularly from about 100 µg/mL to about 1000 µg/mL, even more particularly from about 125 µg/mL to about 250 µg/mL. An $IC_{50}$ of 179 µg/mL was observed for the cashew testa extract.

The above data illustrates that the botanical extract of the testa of Anacardium occidentale L. has one or more compounds that may have some contributions in addressing the imbalance between the normal physiological condition and uncontrolled enzymatic expression/activity at the time of tissue remodeling or repair, that is, the extract exhibits modulation of one or more metabolic disorders.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Further, unless defined otherwise, all technical and scientific terms used herein have the same meaning as commonly understood to one of ordinary skill in the art to which this invention belongs. Consequently, it is not intended that this invention be limited to the specific embodiments disclosed herein, but that it cover all modifications and alternatives coming within the true scope and spirit of the invention as embodied in the attached claims.

We claim:

1. A method of modulating one or more metabolic disorders in a subject comprising:
    administering a composition comprising a botanical extract of the testa of Anacardium occidentale L.,
    wherein the botanical extract has been standardized to a catechin content of about 15.0 w/w % or greater, based on total weight of the extract, and
    wherein the botanical extract is present in the composition in an amount of from about 15.0 µg/mL to about 250.0 µg/mL.

2. The method according to claim 1, wherein the composition is a dietary supplement.

3. The method according to claim 1, wherein the dietary supplement is in solid dosage form and the carrier is chosen from gelatin, starch, magnesium stearate, talc, gums, silicon dioxide, stearic acid, cellulose and combinations thereof.

4. The method according to claim 1, wherein the composition is effective in inhibiting the expression of MMP-9.

5. The method according to claim 1, wherein the composition exhibits PPAR-γ agonist activity.

* * * * *